United States Patent
Yi et al.

(10) Patent No.: US 9,550,609 B2
(45) Date of Patent: Jan. 24, 2017

(54) CONTAINER WITH A SEAL AND A METHOD OF MAKING THE SEAL

(71) Applicant: GE Healthcare Bio-Sciences AB, Uppsala (SE)

(72) Inventors: Shujian Yi, Westborough, MA (US); Rolf Hjorth, Uppsala (SE); David Ronnholm, Marsta (SE); Thomas Falkman, Uppsala (SE)

(73) Assignee: GE Healthcare Bio-Sciences AB, Uppsala (SE)

( * ) Notice: Subject to any disclaimer, the term of this patent is extended or adjusted under 35 U.S.C. 154(b) by 0 days.

(21) Appl. No.: 14/410,595

(22) PCT Filed: Jun. 20, 2013

(86) PCT No.: PCT/SE2013/050747
§ 371 (c)(1),
(2) Date: Dec. 23, 2014

(87) PCT Pub. No.: WO2014/003641
PCT Pub. Date: Jan. 3, 2014

(65) Prior Publication Data
US 2015/0367992 A1   Dec. 24, 2015

(30) Foreign Application Priority Data
Jun. 27, 2012  (SE) ................... 1250703-4

(51) Int. Cl.
*B65D 33/02* (2006.01)
*B29C 65/48* (2006.01)
(Continued)

(52) U.S. Cl.
CPC ............. *B65D 33/02* (2013.01); *B29C 65/02* (2013.01); *B29C 65/10* (2013.01); *B29C 65/48* (2013.01);
(Continued)

(58) Field of Classification Search
CPC ....... B65D 33/02; B65D 25/14; B65D 90/046; B65D 90/04; B65D 7/38; B65D 7/34; B65D 1/0215; B65D 1/0207; B29C 65/103; B29C 65/10; B29C 65/02; B29C 65/4835; B29C 65/483; B29C 65/4805; B32B 27/06; B32B 27/08
(Continued)

(56) References Cited

U.S. PATENT DOCUMENTS 2,177,919 A * 10/1939 Vogt ......................... B65D 5/60
                                                          141/10
2,298,522 A    10/1942 Waters
(Continued)

FOREIGN PATENT DOCUMENTS

EP    1454835 A1    9/2004
EP    1714567 A2    10/2006
(Continued)

OTHER PUBLICATIONS

International Search Report and Written Opinion dated Oct. 4, 2013 which was issued in connection with PCT Patent Application No. SE2013/050747 which was filed on Jun. 20, 2013.

*Primary Examiner* — Robert J Hicks
(74) *Attorney, Agent, or Firm* — Wood IP LLC

(57) ABSTRACT

A container comprising a first material and a second material, the first material being a flexible material and the second material being a rigid or semi-rigid material and at least partially defining an interior compartment for keeping a fluid inside the container characterized in that the flexible material and/or the semi-rigid or rigid material have thermoplastic properties and wherein the flexible material and the semi-rigid or rigid material are joined together by a seal or joint which comprises a heat seal and an adhesive seal.

10 Claims, 3 Drawing Sheets

(51) Int. Cl.
  *B29C 65/72* (2006.01)
  *B29C 65/02* (2006.01)
  *C12M 1/00* (2006.01)
  *B29C 65/10* (2006.01)
  *B29C 65/00* (2006.01)
  *B29L 31/00* (2006.01)
  *B29K 101/12* (2006.01)

(52) U.S. Cl.
  CPC .......... *B29C 65/4835* (2013.01); *B29C 65/72* (2013.01); *B29C 66/12441* (2013.01); *B29C 66/47421* (2013.01); *B29C 66/542* (2013.01); *B29C 66/7315* (2013.01); *B29C 66/7392* (2013.01); *C12M 23/14* (2013.01); *B29C 65/482* (2013.01); *B29C 65/4815* (2013.01); *B29C 65/4845* (2013.01); *B29C 66/71* (2013.01); *B29C 66/73921* (2013.01); *B29K 2101/12* (2013.01); *B29K 2995/0082* (2013.01); *B29L 2031/712* (2013.01); *B29L 2031/7128* (2013.01)

(58) Field of Classification Search
  USPC ......... 220/613, 612, 610, 678, 359.4, 359.1, 220/62.22, 62.21, 62.11, 677; 156/60; 428/35.7; 215/12.2, 12.1
  See application file for complete search history.

(56) References Cited

U.S. PATENT DOCUMENTS

| | | | | | |
|---|---|---|---|---|---|
| 2,307,902 | A | * | 1/1943 | Vogt | B65D 5/60 383/106 |
| 2,711,781 | A | * | 6/1955 | Langer | B29C 65/18 156/290 |
| 2,956,915 | A | * | 10/1960 | Korn | B32B 27/00 220/565 |
| 2,989,208 | A | * | 6/1961 | Gibbs, Jr. | B65D 15/06 220/254.2 |
| 3,238,077 | A | * | 3/1966 | McCulloch | B29C 70/00 156/334 |
| 3,921,897 | A | * | 11/1975 | Noyes | B65D 25/16 206/461 |
| 4,837,849 | A | * | 6/1989 | Erickson | B29C 65/7437 383/104 |
| 4,994,310 | A | * | 2/1991 | Frisk | B32B 27/08 427/404 |
| 5,256,105 | A | | 10/1993 | Austin | |
| 6,391,407 | B1 | * | 5/2002 | Kashiba | B32B 27/18 252/188.28 |
| 6,576,337 | B1 | | 6/2003 | Radford-Hancock | |
| 2005/0031812 | A1 | * | 2/2005 | Suzuki | B29C 45/14336 428/35.2 |
| 2006/0165939 | A1 | | 7/2006 | Hottner | |
| 2008/0044614 | A1 | | 2/2008 | Hannon | |
| 2011/0066218 | A1 | | 3/2011 | Geibel | |

FOREIGN PATENT DOCUMENTS

| | | |
|---|---|---|
| EP | 1714567 A3 | 9/2007 |
| EP | 1842800 A2 | 10/2007 |
| GB | 2419381 A | 4/2006 |
| JP | 11297286 A | 10/1999 |
| WO | 9809872 A2 | 3/1998 |
| WO | 9919222 A1 | 4/1999 |
| WO | 2009153558 A1 | 6/2009 |

* cited by examiner

CONTAINER WITH A SEAL AND A METHOD OF MAKING THE SEAL

CROSS-REFERENCE TO RELATED APPLICATIONS

This is a national stage application under 35 U.S.C. §371(c) of prior-filed, co-pending, PCT application serial number PCT/SE2013/050747, filed on Jun. 20, 2013, which claims priority to Swedish patent application serial number 1250703-4, filed on Jun. 27, 2012, the entire contents of which are incorporated by reference herein.

TECHNICAL FIELD

Embodiments of the present invention relate to a technical field of containers comprising a flexible material and a rigid or semi-rigid material. Especially, embodiments of the present invention relate to a seal between the rigid or semi-rigid material and the flexible material and to a method of making the seal.

BACKGROUND

Single-use or disposable systems are rapidly increasing in biopharmaceutical industry due to the flexibility and cost-effectiveness of such systems. Disposable components in the systems are presterilized and qualified to regulatory requirements. Disposable systems are easy to adapt to different production purposes and it is easy and inexpensive to change a product line while good process reliability is at least maintained or even improved.

There are several kinds of biopharmaceutical systems, such as mixing systems, in which disposable containers or bags may be used. These containers or bags are made of sheets of flexible material, such as plastic, plastic laminates or corresponding materials.

One type of mixing systems in which such containers can be used is a bioreactor system in which cells or microorganisms can grow. Mixing systems include also systems used to prepare for example buffer and media.

Mixing systems may comprise a support or vessel which supports or houses a disposable bag or container of the above-mentioned type. The support may be a support plate or tray for a bioreactor bag of a kind used in GE Healthcare WAVE Bioreactor$^{TM}$ systems. The vessel may be a tank-type support which has a substantially cylindrical form, for example substantially circular cylindrical and is made of rigid material such as stainless steel to provide sufficient support for a flexible bag or container. The flexible container or bag is placed on the tray or in the inside of the vessel in an accurate manner so that for example different pipelines or tubes, mixers and sensors can be connected to the bag properly and accurately. US2011/0310696 and EP1842800 disclose mixing systems of this kind As mentioned above, disposable containers are often mainly made of sheets of flexible materials. To stabilize or reinforce the containers or to enable the connection of different pipelines or sensors to the containers they may comprise parts of rigid or semi-rigid materials. These rigid or semi-rigid parts provide a platform for safe and secure attachment of for example sensors, pipelines for fluids (both gas and liquid) and mixers. Further, the rigid or semi-rigid parts can reinforce and stabilize the containers and therefore facilitate placing of the containers into mixing vessels in accurate manner.

However, seals between rigid/semi-rigid and flexible materials may involve a safety risk, since the seals may be weak and thereby cause leakage of the liquids in the container and/or contamination of the liquids inside the container by the surrounding environment. Therefore, it is essential that the risk for leakage and/or contamination can be minimized and the seal between these different materials can be made as safe and secure as possible.

Containers may vary in size from about 1 liter to about 2000 liters and especially, if containers are large and leakage occurs from the material seals, there may be catastrophic consequences both in respect of loss of material and consequences to the surrounding environment, since the liquids leaked may cause damage to the surrounding equipment, such as control computers. Of course, the leaked liquid has to be cleaned which is both expensive and labour consuming.

Another problem which may occur in the seals of traditional type is micro leakage, i.e. leakage in very small amounts which is due to the unevenness of the sealing. Micro-leakage may cause contamination of sensitive cultivations and also on the other hand the environment surrounding the cultivation.

SUMMARY OF THE INVENTION

The object of the present invention is to provide a seal or joint between flexible material and rigid or semi-rigid material in containers which is safe and even in such a way that the risk for leakage or micro leakage is minimized. The seal or joint of the present invention also minimizes the risk for breakage of seals or joints in the containers.

The objects above are obtained by a container according to the present invention comprising a first material and a second material, the first material being a flexible material and the second material being a rigid or semi-rigid material and which container at least partially defines an interior compartment for keeping a fluid inside the container. The flexible material and/or the semi-rigid or rigid material have thermoplastic properties and the flexible material and the semi-rigid or rigid material are joined together by means of a seal or joint which comprises a heat seal and an adhesive seal.

The present invention further relates to a method of providing the seal.

Further objects and advantages will be described in more detail in the following detailed description of the invention.

BRIEF DESCRIPTION OF THE DRAWINGS

The present invention will be discussed in detail below with reference to the attached drawings. The embodiments shown in the figures are purely examples and should not be regarded as limiting the present invention in any way.

DETAILED DESCRIPTION

Figure 1:
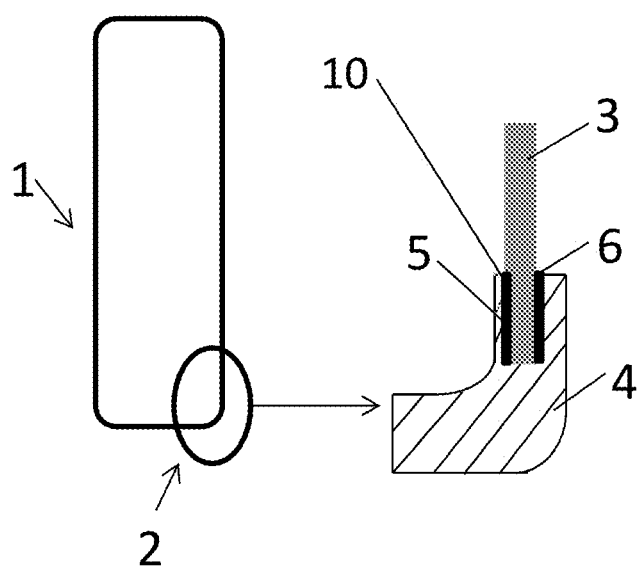
FIG. 1 schematically shows an example of a container and an enlarged view in cross section of the seal/joint section in a container.

In FIGS. 1-4 examples of products with seals according to the present invention are shown. The skilled person realizes however that for example the container 1 shown in FIG. 1 may have another form or be of another type as long as the container comprises a first material and a second material wherein the first material is a flexible material and the second material is a rigid or semi-rigid material and wherein the container at least partially defines an interior compartment for keeping a fluid, which can be both liquid or gas, inside the container. At least one of the flexible material and the semi-rigid or rigid material has thermoplastic properties so that it is possible to form a heat seal between the materials. In an embodiment, both of the materials have thermoplastic properties or comprise components having thermoplastic properties to facilitate and improve the sealing properties of the heat seal. The flexible material and the semi-rigid or rigid material are joined together by means of a seal or joint which comprises both the heat seal and an adhesive seal. The interior compartment may be defined by both the first and the second material.

By flexible material is meant materials which can be easily bent without breaking The flexible material may have a thickness of less than 1 mm, suitably of from about 0.005 mm to about 0.7 mm, and, in an embodiment, of from about 0.01-0.5 mm depending on the size and form of the container or bag. The flexible material may have a flexural modulus according to ASTM D790 of less than 2000 MPa. The flexibility of the material is further defined by the thickness of the material, i.e. basically that the thinner the material the more flexible the material. However, two materials of equal thickness may have different flexibility due to the differences in flexural modulus of the materials.

The flexible material may be a polymeric film material and can be made of a mono layer material or a laminate comprising two or more layers, e.g. polymeric material films. The flexible material comprises at least one layer of a polymeric film material having thermoplastic properties. The polymeric film material should be sterilizable and, in an embodiment, resists gamma radiation, i.e. it substantially retains its properties after gamma radiation. Suitable materials may be conventional film materials used in packaging industry and, in an embodiment, for example mono layer or multi layer PE (polyethylene), ULDPE (Ultra Low Density Polyethylene), LLDPE (Linear Low density Polyethylene), EVOH (Ethylene Vinyl Alcohol) and PA (polyamide). The material may also be a laminate film comprising one or more polymeric materials or the material may be for example multi layer coextruded polyethylene film, such as ULDPE/EVOH/PE/PA. The laminate film may be further comprised of two or more material layers of different thermoplastic materials which have different melting points. In an embodiment, the thermoplastic material facing the interior of the container has a lower melting point than the side facing outwards. In this way, it can be assured that only the interior side of the laminate is heat-sealed. However, the mentioned flexible materials are only examples of suitable materials and any flexible material with thermoplastic properties which fulfils product requirements can be used.

By rigid or semi-rigid material is meant material which is unbending or may be slightly bent, i.e. it has slightly flexible and/or elastic properties. The flexural modulus of the rigid material is, in an embodiment, greater than 200 MPa according to ASTM D790. The flexural modulus value may be overlapping with the flexural modulus value of the flexible material, but the rigidity of the material is further defined by the thickness of the material. The rigid material has a thickness of from 1 mm. There is no upper limit for the thickness of the rigid material. The rigid or semi rigid material is further substantially dimensionally stable and is, in an embodiment, moldable and can be a polymeric material. Examples of suitable materials are for example low density polyethylene or high density polyethylene materials, polyamide or polypropylene. Further, the rigid or semi rigid material may be a composite material comprising a polymer matrix, such as as polyester, vinyl ester, polyamide polypropylene or any other moldable polymer material. The polymer material, in an embodiment, has thermoplastic properties and is sterilizable and, in an embodiment, resists gamma radiation, i.e. it substantially retains its properties after gamma radiation. The rigid parts can be for example vacuum formed or molded for example by injection molding. The adhesives used in the adhesive seal are, in an embodiment, medical grade adhesives. The adhesives can be for example hot-melt adhesives, UV-curable adhesives or solvent-based adhesives. The hot-melt adhesives used should, in an embodiment, have a lower melting point than the flexible film material so that the flexible film does not melt when the hot-melt adhesive is applied to the material. Examples of adhesives are for example epoxy- or silicone-based adhesives, such as MasterBond X17 and 3M DP8005. Further, for example adhesive tape could be used.

The heat seal is obtained by bringing the flexible material in contact with heat, so that the thermoplastic component in the material melts and provides the heat seal. The heat seal may be obtained by any suitable manner, which are per se known to the skilled person, for example by hot air welding or conventional heat mold sealing.

There are several advantages obtained by the seal according to the present invention. For example, when the heat seal is located on the liquid side of the container, exposure of a tie layer to the liquid can be prevented. Adhesives are complex products with respect to for example curing properties and a risk for micro leakage is increased if only adhesive seal is provided. Because of the heat seal, the film is mechanically interlocked in the rigid bottom, and there is less tendency of seal delamination. The adhesive seal provides a supplementary seal with other properties. For example if the adhesive cures by chemical cross-linking, it will not be so sensitive to temperature changes and it provides a flexible sealing which does not brake easily. Thus the two different seals together provide an excellent sealing result while the liquid in the container is not contaminated by the environment or by the adhesives used for the seal.

In an embodiment, the rigid or semi-rigid material comprises a trench or a recess into which the flexible material is arranged. This enables sealing of the flexible material and the rigid material in such a way that opposite sides of the film are provided with different seals, i.e. the heat seal is located on one side of the flexible material and the adhesive seal is located on the side opposite side of the flexible material. The seal may be difficult to make by heat only because of the large difference between properties, e.g. melting temperature, of a polymer film and molded rigid or semi-rigid parts. Often, the film is melted but the molded parts are not due to low heat conduction of polymer materials. Therefore, the additional seal with adhesive provides a secure seal between the two different materials. The trench or recess is adapted to the product and it may be a groove having depth of from about 1 mm to about 100 cm, depending on the size of the container and/or the purpose of the seal. The width and length of the trench are adapted to the dimensions of the flexible material or film and are close to the dimensions of the film so that the application of the adhesive and performing the heat seal are possible. Further advantages of the trench are that it improves the mechanical stability and strength to the joint, that it provides fixation of the film during the sealing operations and that it can be designed to prevent contact between the adhesive and the liquid inside the container.

In an embodiment, the heat seal is located on the side facing the interior of the container and the adhesive seal is located on the side facing outwards. This ensures that the liquids inside the container do not come into contact with the adhesive, and thus it is possible to use different kinds of adhesives.

The rigid or semi-rigid material can be used for several purposes in the container. For example it can be used as a platform for a sensor coupling or a tube coupling. The rigid or semi-rigid material can be also used to form a reinforcement portion for the container. Especially, this reinforcement portion can be formed to be a bottom and/or a top part of the container.

The present invention further relates to a method of providing a seal or joint between the flexible material and the rigid or semi-rigid material wherein the flexible material and/or the semi-rigid or rigid material have thermoplastic properties comprising the steps of: providing a trench in the semi-rigid or rigid thermoplastic material to receive an edge portion of the flexible material, providing an adhesive on the flexible material, inserting the flexible material into the trench, and solidifying the adhesive heat-sealing the side opposite to the side of the flexible material comprising the adhesive.

As already mentioned above, the heat seal can be provided by hot-air or hot-mold sealing. When the film is inserted into the trench or recess of the rigid material, the adhesive can be applied to side facing outwards from a liquid. After the adhesive is solidified by for example chemical reaction or solvent evaporation, it will fix the film to the rigid material. Then the inside seal can be prepared by hot air or heat mold seal. The multilayer film may have a construction in which the fluid contact layer has a lower melting point than the opposite side facing outwards and therefore, the fluid contact layer can be easily welded to the molded rigid or semi-rigid parts by heat. Because the heat transfer occurs in the inner surface and the laminate has a low heat conductivity, the inner surface is capable to weld the inner interface while the outer interface is still solid. Hence, the joint or seal can be prepared in two steps: the first step can be adhesive bonding of the outer layer to the molded parts, and the second step can be heat welding or molding a seal between fluid contact layer and the molded rigid or semi-rigid parts. Of course it could be possible to first prepare the adhesive seal and after that the heat seal.

The present invention is further illustrated in the figures as described below.

FIG. 1 shows a container 1 comprising a flexible material 3, i.e. a plastic film, and a semi-rigid material 4. The flexible material forms a side wall of the container 1, while the semi-rigid material 4 forms a bottom part of the container to stabilize and reinforce the container 1. The position of the seal/joint between the two materials is depicted by 2 and an enlarged view is shown to the right of the container 1. A trench 10 is formed into the rigid material into which the film 3 is placed. The seal/joint comprises a heat seal 5 on the interior side of the container and an adhesive seal 6 on the opposite, outer side of the container 1.

Figure 2:
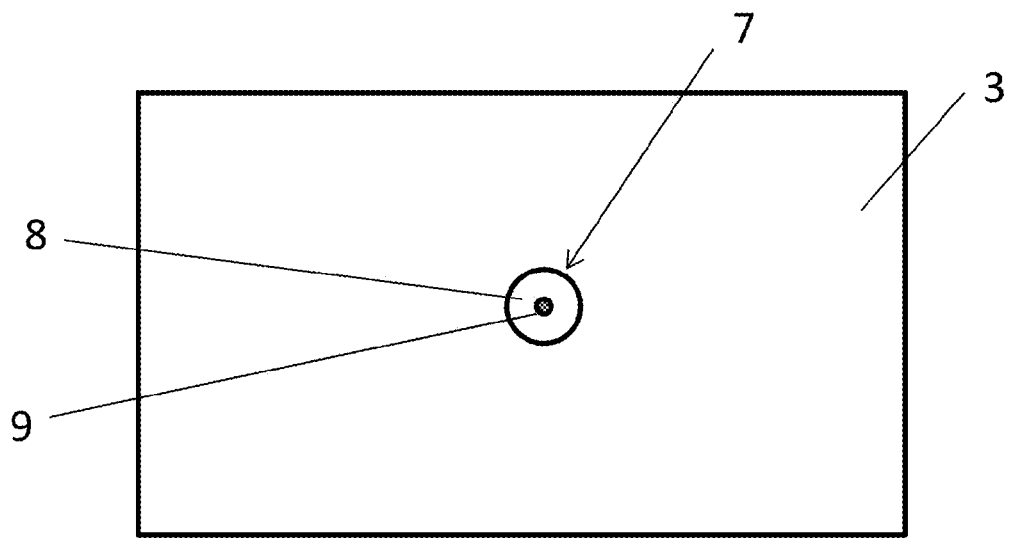
FIG. 2 schematically shows a top view of a plastic film having a circular platform for a sensor or tube coupling as further shown in more detail in FIGS. 3 and 4

FIG. 2 shows a top view of another type of container, namely a flexible bag, which is flat in an inflated condition but obtains a three-dimensional, pillow-like form in an inflated condition (not shown). The container is mainly made of a flexible material 3, such as a plastic film. The container comprises further a circular platform 7 of a rigid material, such as rigid plastics, which can be used to couple a sensor or a tube to the container, as shown more in detail in FIGS. 3 and 4. The platform 7 comprises a rigid material base 8 and a slot or hole 9, which can be a through hole or which may comprise a membrane.

Figure 3:
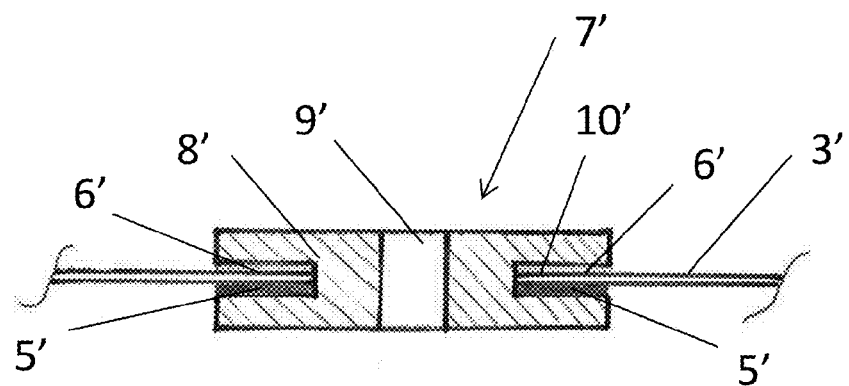
FIG. 3 schematically shows an example of a sensor coupling in enlarged, view in cross section and of the seal/joint between the sensor coupling and a flexible film.

FIG. 3 shows in more detail a structure of the platform 7'. The platform comprises rigid base material 8' and a through hole 9' which can receive for example a sensor probe. Sensors may be placed inside the hole and a sensor probe or sensing material may be in contact with the fluid inside the container in an appropriate manner either invasively or non-invasively. The flexible film 3' is placed inside a trench 10' in the base material 8' and a heat seal 5' is provided on the lower side of the film 3', and an adhesive seal 6' is provided on the upper side of the film 3'. The lower side of the film 3' is aimed to be placed so as to form the inside of a container, and the upper side of the film 3' is aimed to form the outside of the container.

Figure 4:
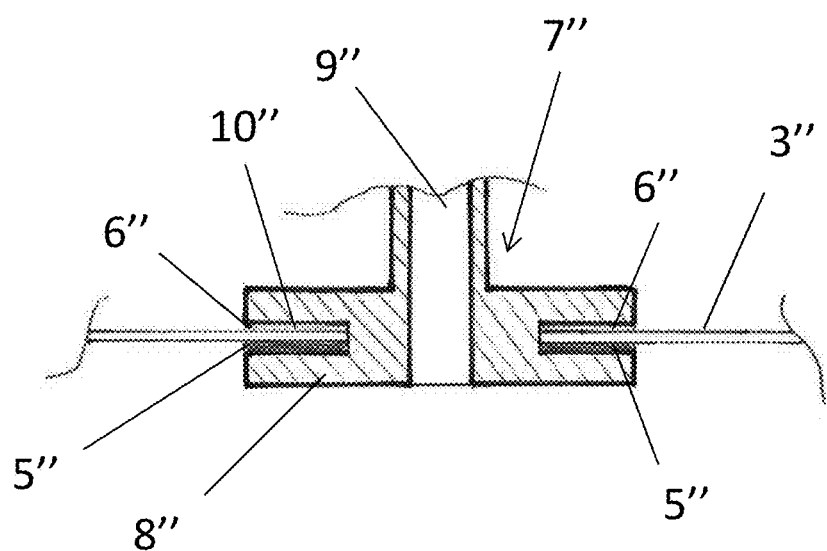
FIG. 4 schematically shows an example of a tube coupling in enlarged, partial view in cross section and of the seal/joint between the tube coupling and a flexible film.

FIG. 4 shows another example of a platform. This platform 7" can be used for example for tube couplings. Tubes are necessary to be able to feed or harvest fluids inside the container. The tubes may be integral with the platform, or they may be connected to the platform by coupling means (not shown). Such couplings are known in the art and are therefore not explained more in detail in this application. The platform comprises rigid base material 8" and a through hole 9", so that a fluid can be fed or harvested into or out of the container. The flexible film 3" is placed inside a trench in the base material 8" and a heat seal 5" is provided on the lower side of the film 3", and an adhesive seal 6" is provided on the upper side of the film 3". The lower side of the film 3" is aimed to be placed so as to form the inside of a container, and the upper side of the film 3" is aimed to form the outside of the container.

The platforms 7, 7' and 7" can be formed as one piece, but they could also be formed of two or more pieces which are connected together in an appropriate way, e.g. by means of mechanical connecting means (e.g. snap connectors, bayonet connectors, screws, etc.), by gluing or by welding .

It is clear that the platforms of the type shown in FIGS. 3 and 4 can be used in containers as shown in FIGS. 1 and 2.

The examples above should not be considered limiting the invention in any way. Instead the scope of the invention is limited by the appended claims.

The invention claimed is:
1. A container, comprising a first material, and a second material,
   wherein the first material is a flexible material, and the second material is a rigid or semi-rigid material and the first material at least partially defining an interior compartment for keeping a fluid inside the container,
   wherein the flexible material and/or the rigid or semi-rigid material have thermoplastic properties, and
   wherein the rigid or semi-rigid material comprises a rabbet trench into which the flexible material is arranged such that a heat seal located on the side facing an interior of the container is in-between and connects the first material and the second material and an adhesive seal located on a side facing exterior of the container such that the adhesive seal is in-between and connects the first material and the second material.

2. The container according to claim 1, wherein the flexible material is a laminate film.

3. The container according to claim 2, wherein the flexible material is comprised of two or more material layers of different thermoplastic materials and the thermoplastic materials have different melting points.

4. The container according to claim 2, wherein the laminate film comprises at least two plastic material layers which layers are of different plastic materials relative to each other.

5. The container according to claim 3, wherein the thermoplastic facing the interior of the container has a lower melting point than the side facing outwards.

6. The container according to claim 1, wherein the rigid or semi-rigid material is used as a platform for sensor coupling or tube coupling.

7. The container according to claim 1, wherein the rigid or semi-rigid material forms a reinforcement portion for the container.

8. The container according to claim 7, wherein the reinforcement portion is formed of a bottom and/or a top of the container.

9. A method of providing the seal between the flexible material and the rigid or semi-rigid material in the container of claim 1, the method comprising: providing a trench in the rigid or semi-rigid thermoplastic material edge portion of the flexible material;

providing an adhesive on the flexible material; inserting the flexible material into the trench; solidifying the adhesive; and heat-sealing the side opposite to the side of the flexible material comprising the adhesive.

10. The method according to claim 9, wherein the heat-seal is provided by hot-air or hot-mold seal.

* * * * *